United States Patent [19]

Warrin et al.

[11] Patent Number: 4,820,152

[45] Date of Patent: Apr. 11, 1989

[54] SINGLE MULTI-FUNCTION HANDPIECE FOR DENTAL INSTRUMENTS

[75] Inventors: George E. Warrin, North Merrick; Rene J. Perdreaux, Brooklyn; Richard H. Paschke, Medford; Teodor E. Constantinescu, Astoria; Robert McGill, Carona, all of N.Y.

[73] Assignee: Dentsply Research & Development Corp., Milford, Del.

[21] Appl. No.: 40,649

[22] Filed: Apr. 21, 1987

[51] Int. Cl.[4] .................................................. A61C 1/07
[52] U.S. Cl. .................................... 433/86; 433/88; 433/89; 433/119; 219/10.65; 307/309; 328/5; 239/135; 239/424
[58] Field of Search ..................... 433/80-86, 433/88, 118, 119; 219/10.65; 239/135, 424; 307/308, 309; 328/5

[56] References Cited

U.S. PATENT DOCUMENTS

| Re. 28,752 | 3/1976 | Balamuth et al. . | |
|---|---|---|---|
| 2,192,661 | 3/1940 | Jones | 239/424 |
| 2,641,839 | 6/1953 | Black . | |
| 2,904,664 | 9/1959 | Rothacker | 219/10.65 |
| 3,522,801 | 8/1970 | Robinson . | |
| 3,636,947 | 1/1972 | Balamuth . | |
| 3,645,255 | 2/1972 | Robinson . | |
| 3,921,044 | 11/1975 | McShirley | 433/118 |
| 3,956,826 | 5/1976 | Perdreaux, Jr. . | |
| 4,116,239 | 9/1978 | Ewen . | |
| 4,169,984 | 11/1979 | Parisi . | |
| 4,330,278 | 5/1982 | Martin . | |
| 4,412,402 | 11/1983 | Gallant . | |
| 4,428,748 | 1/1984 | Peyman et al. . | |
| 4,462,803 | 7/1984 | Landgraf et al. . | |
| 4,482,322 | 11/1984 | Hain et al. . | |
| 4,487,582 | 12/1984 | Warrin . | |
| 4,492,574 | 1/1985 | Warrin et al. | 433/81 |
| 4,492,575 | 1/1985 | Mabille . | |
| 4,494,932 | 1/1985 | Rzewinski | 433/88 |
| 4,522,597 | 6/1985 | Gallant . | |
| 4,540,365 | 9/1985 | Nelson et al. . | |
| 4,608,018 | 8/1986 | Ghedini et al. . | |
| 4,631,871 | 12/1986 | Saunders . | |
| 4,676,749 | 6/1987 | Mabille | 433/88 |

FOREIGN PATENT DOCUMENTS

| 520071 | 12/1955 | Canada | 433/88 |
|---|---|---|---|
| 2219761 | 10/1973 | Fed. Rep. of Germany | 433/118 |

Primary Examiner—Carroll B. Dority, Jr.
Attorney, Agent, or Firm—David E. Wheeler; Edward J. Hanson, Jr.

[57] ABSTRACT

A single handpiece that can be used in multiple dental treatments is provided. The handpiece comprises a housing having a coil for producing an electromagnetic or electrostrictive field in the housing, and a number of inserts that react with the electromagnetic or electrostrictive field and can be used with the housing to complete the handpiece. A switching system used with the handpiece, which electrically recognizes the particular insert used with the housing provide for automatically controlling circuitry that determines which of a number of materials and medicaments are to be delivered to the handpiece for use with a particular insert. Circuitry which provides better control of the ultrasonic insert in the handpiece is also provided.

28 Claims, 4 Drawing Sheets

SINGLE MULTI-FUNCTION HANDPIECE FOR DENTAL INSTRUMENTS

BACKGROUND OF THE INVENTION

The present invention relates to a single handpiece for dental instruments that can be used for ultrasonic scaling when used with an ultrasonic scaling insert, and can be used to abrasively clean teeth when used with an air-abrasive insert. A unique switching system makes possible the use of a number of different kinds of inserts in the same handpiece. A method and apparatus for precise control of magnetostrictive and/or electrostrictive transducers is also provided. The method and apparatus for control of the transducer is discussed with reference to a dental prophylaxis unit; however, it is applicable to any application which requires the precise control of electrical, mechanical or electro-mechanical systems.

1. PRIOR ART

Warrin et al, in U.S. Pat. No. 4,492,574 teach an ultrasonic endodontic dental handpiece having a coil for establishing an alternating magnetic field, the housing having a cooling fluid inlet at one end and being open at the other end for receiving and supporting a removable insert.

Rzewinski, in U.S. Pat. No. 4,494,932 teaches an apparatus for dispensing cleaning powder in an air stream to be directed onto the surface of teeth. The apparatus includes a fluid tight chamber for containing a supply of cleaning powder. Air under pressure is directed into the chamber, and an outlet in the sidewall of the chamber permits air and powder to flow out under pressure.

2. BACKGROUND

Stains on teeth may originate from various sources or causes including smoking, tobacco chewing, excessive drinking of tea or from vegetable origin. Calculus is of several different types, especially serumal and salivary, and calculus deposits ordinarily accumulate in pockets between the teeth and the surrounding soft tissues, the serumal calculus originating from the saliva. These constituents precipitate and bond themselves to the exposed tooth surfaces.

Various techniques and equipment are already known and used in the cleaning of teeth, including hand instruments, rotary rubber cups carrying an abrasive paste of pumice for example, all of which techniques may be used effectively in the removal of calculus, but none of which techniques are satisfactory in effecting the removal of various types of stain, especially the removal of stain from broad areas of the teeth.

It is known in the art to clean teeth using ultrasonic scaler inserts. In an ultrasonic scaler, vibrational motion of a transducer is transformed to flexural or elliptical motion of an insert tip. This motion of the tip is used to dislodge calculus from the teeth. The scaler also has means for irrigating the area where the scaler tip is used by dispensing a liquid, most frequently water, through or over the surface of the scaler tip.

It is also known in the art to clean teeth using air-abrasive equipment which is particularly useful for removing stains from crevices in the teeth.

In the use of air-abrasive equipment for dental purposes, the delivery and dispersal of abrasive particles in air suspension in the mouth is objectionable and in some prior equipment employed for tooth cutting, vacuum means has been employed to capture the abrasive particles. This, however, is bulky and cumbersome. In some prior systems it has also been contemplated to wash the teeth with water following the abrasive treatment, but such subsequent washing does not overcome the objectionable initial distribution of the abrasive particles on the soft tissues and other parts of the mouth. To overcome these difficulties and to provide air-abrasive prophylaxis equipment adapted to the convenient and effective removal of stain and or calculus in a manner which is simple and which produces minimum discomfort to the patient, a handpiece was provided having a nozzle with an air-abrasive discharge passage, and a water discharge passage surrounding the air-abrasive passage, together with control means by which warmed water was delivered for discharge through the water passage, and the air-abrasive and water streams were coordinated to capture the abrasive particles after they were dispensed.

In the handpiece provided in the prior art, the water discharge passage is directed to impinge upon the surface of the tooth being cleaned in an area immediately adjacent to or overlapping the area of impingement of the air-abrasive stream. Preferably a water stream is provided to form a curtain surrounding the air-abrasive stream. In its most effective embodiment, the motion of the powder and liquid as it is being dispensed from the handpiece causes a mixing of the powder and water to form a slurry. It is a slurry of polishing powder and water which provides the most effective cleaning of teeth.

The practitioner has found it most convenient and effective to use both the ultrasonic scaler and the air-abrasive systems described above to provide prophylactic treatment of the teeth. Using both systems, however, requires two sets of equipment, or at least two handpieces: a handpiece for ultrasonic scaling for calculus and plaque removal, and a second handpiece for air-polishing stain and plaque removal. In addition, a water heater is desirable for use with the air-abrasive portion of the device. Since space is usually at a premium in the operatory, the disadvantages of using the described equipment is apparent. In addition, it is bothersome and time consuming for the practitioner to change handpieces in the middle of a treatment.

The prior art systems for driving the scaler insert of the handpiece comprise a magnetostrictive transducer, a signal generator, a power supply and some form of feedback.

The known feedback systems can be divided into three classes. In the simplest form of feedback, the voltage is a function of frequency and is related to the sum of all internal phase shifts. This form of feedback is practical for use only in high quality transducers designed to operate at a specific frequency range in which the induced voltage values are small.

Systems which rely on purely electrical feedback comprise a second feedback system. These two systems have the following shortcomings:
1. The system may start up in either of two different phase conditions, resulting in very different mechanical outputs.
2. In one of the possible phase conditions, impedence in the system may cause reactance in the no-load condition resulting in reduced start-up capability.
3. If the system must be capable of handling high loads, it usually operates with reduced efficiency at lower loads.

4. The tuning of the system must always be a compromise between higher efficiency and start up requirements.

The third system utilizes a velocity feedback measurement. In this system the vibration pick up voltage controls a generator whose gain is a function of the voltage across the load and the velocity difference between the two ends of the mechanical resonator.

In this system the velocity feedback is either resonated or otherwise wave shaped to provide unambiguous frequency information to the amplifier. It is said in the prior art that this is a requirement to utilize the velocity pick up signal.

It is the object of the present invention to overcome the above described difficulties with the prior art.

SUMMARY OF THE INVENTION

The present invention provides a single multi-function handpiece for ultrasonic scaling and abrasive stain and plaque removal from teeth. The handpiece of this invention has an elongated housing and a coil in said housing for establishing an alternating electromagnetic field. The housing preferably has at least one inlet for introduction of a liquid therein, and at least one inlet for introduction of a powder therein. The housing has an open end adapted for placing an insert into the housing with a sealing fit. The housing is adapted to use at least an ultrasonic scaler insert and an air-abrasive insert. The handpiece also provides a switching signal means or sensor for recognizing the type of insert present in the housing and for controlling electrical circuitry and/or other switching means for controlling the correct combination of air, powder and water that is desired to be delivered to the handpiece for use in conjunction with the insert used.

The invention also includes an insert for use in the handpiece which has a magnetically activated heating element and a nozzle for dispensing an abrasive powder to remove stains and plaque from teeth. The nozzle includes concentric tubing in which the inner tube is used to dispense air and abrasive powder and the outer tube is used to dispense a liquid which forms a slurry with the abrasive powder, the slurry being effective for abrasively cleaning teeth and minimizing the amount of abrasive powder that escapes into the atmosphere. The air-abrasive insert has a magnetic heating element that uses the energy produced by the alternating electromagnetic field in the housing to heat the water used in the treatment.

The invention also includes a contact sensing response activating switching system that controls the impedance of the circuit to activate remote circuitry for controlling the supply of air, powder and water to the handpiece.

Also included in the invention is a method and electronic circuitry for fine tuning the transducer control circuits (coil) so that maximum efficiency is maintained under both low load and high load conditions. The tuning circuit of the invention comprises a feedback system that measures the velocity of the transducer when it is being used, and utilizes those measurements in a phase lock system to provide information to the system for maintaining a consistent mechanical output regardless of the load conditions.

The present invention simplifies the working environment by combining some of the equipment needed for the prophylactic cleaning of teeth into one system. Also, the procedure of cleaning teeth is simplified since the practitioner does not need to interrupt the procedure to change handpieces and to activate a different set of switches to be used with the different handpiece. Using the apparatus of the invention, the practitioner may set out a number of inserts on his tool tray in front of the patient and may simply, easily and quickly change inserts any time during the procedure, and the switching system built into the handpiece will assure that the proper ingredients for use with the insert being used are automatically supplied to the handpiece.

It has been found in the present invention that by operating without modification of a velocity feedback signal, together with unique biasing, the feedback system of the present invention has the following advantages over prior art systems;

1. Precise control of system operation at the maximum mechanical output point.
2. Improved starting both under load and at no-load conditions.
3. Increased acoustic load capability.
4. Allows for manipulation of system parameters.
5. Increased electro-mechanical operating efficiency.
6. System operation point not affected by power supply variations.
7. No tuning control is required.
8. Allows for expanded operating frequency range.

DESCRIPTION OF THE ILLUSTRATED EMBODIMENT

Figure 1:
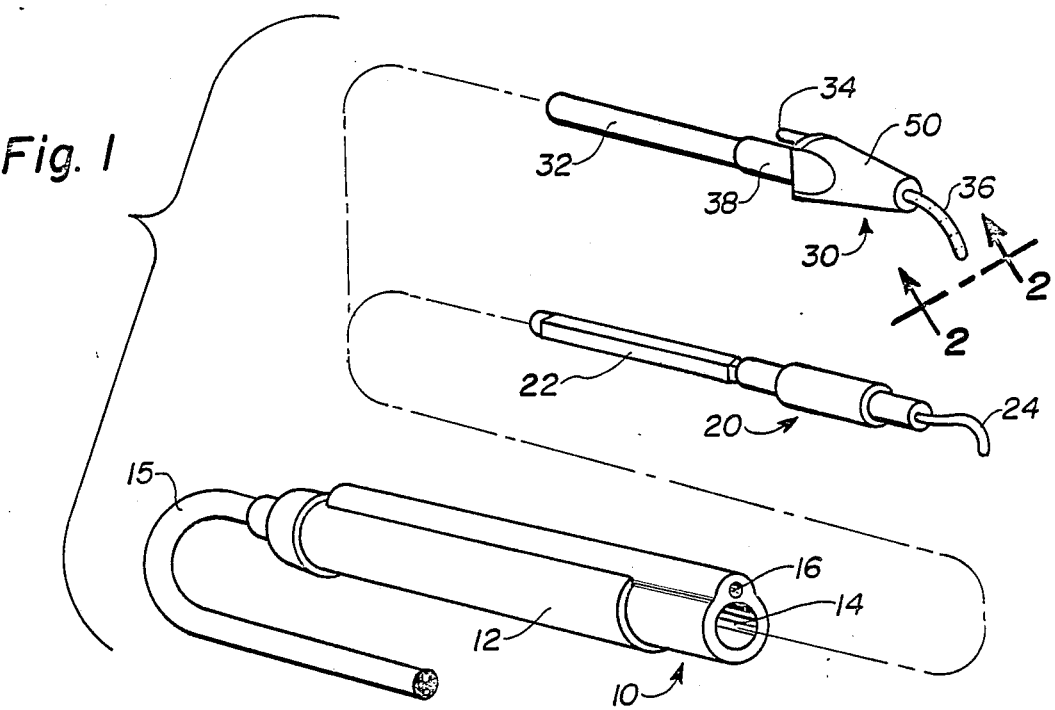
FIG. 1 is a perspective view illustrating the handpiece of the invention together with two inserts that may be used with the handpiece.

With reference now to FIG. 1, the handpiece 10 comprises an elongated housing 12 which has an opening 14 at one end adapted to receive an insert 20 or 30, and cable 15 attached at the opposite end. Cable 15 encloses air and water hoses for delivering air, powder, and water to the handpiece, and all the electrical wires needed to activate and energize the coils in the handpiece.

Powder outlet aperture 16 on housing 12 is adapted to receive powder inlet 34 when air abrasive insert 30 is used in handpiece 10.

The methods of supplying air, powder and water to an air abrasive handpiece are disclosed in U.S. Pat. No. 4,494,932 and references cited therein. The disclosure of U.S. Pat. No. 4,494,932 is incorporated herein by reference. Also, methods of using an ultrasonic endodontic handpiece are described in U.S. Pat. No. 4,492,574 and references cited therein. The disclosure of U.S. Pat. No. 4,492,574 is incorporated herein by reference.

As is known in the art, a scaler insert 20 comprises a transducer stack 22 which interacts with the alternating magnetic field created by, for example, a coil in housing 12, to set up an ultrasonic vibration of the insert. The scaler has a shaped dental tool 24 adapted to scale teeth, and dental tool 24 has means therein for irrigating the work area while dental tool 24 is being used.

The air abrasive insert 30 comprises a heating element 32, and a powder inlet 34 which is adapted to be inserted into powder outlet aperture 16 of housing 12. Water inlet means 38 is provided which permits passage of water over heating element 32 and into nozzle 50. Concentric tubing 36 is part of nozzle 50. In the illustrated embodiment, nozzle 50 comprises a collar that is screwed onto housing 12.

Heating element 32, in the illustrated embodiment, comprises a hollow tubular material which is reactive to a magnetic field. Preferably, the heating element 32 will be a nickel plated tubular ferrous material which utilizes inductive heating to heat water which passes over heating element 32. In general, heat is produced by heating element 32 because the energy from the alternating electromagnetic field creates secondary currents in the heating element 32. This is commonly known as eddy current heating. Water passing over the element is heated and passed through water inlet means 38 through nozzle 50 and into concentric tubing 36.

Similarly, air and powder, from a remote source, pass through housing 12 and into powder inlet 34 and into concentric tubing 36.

Figure 2:
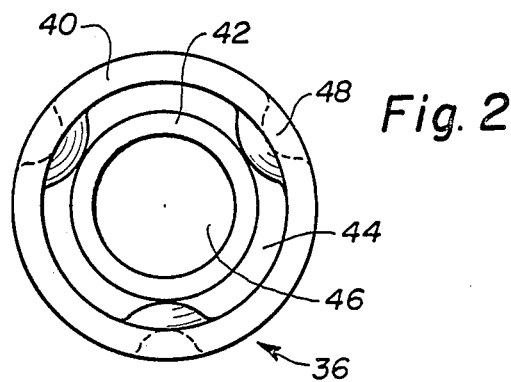
FIG. 2 is an end view of the nozzle of the air-polishing insert of the invention illustrating concentric delivery tubing.

With reference now to FIG. 2, concentric tubing 36 comprises outer tube 40 and inner tube 42. Outer tube 40 is used for delivery of a liquid, such as water through outer orifice 44, and inner tube 42 is used for the delivery of abrasive powder through inner orifice 46. The liquid which passes through outer orifice 44 is used mainly to interact with the air-abrasive powder that is dispensed through inner orifice 46 and form a slurry with the abrasive powder, and this slurry is used to clean the teeth and minimize the escape of abrasive powder into the atmosphere. Those skilled in the art will recognize that the liquid used may also contain medicaments or otherwise be adapted to provide therapeutic activity. Guide means or dimples 48 are included in concentric tubing 36 to maintain the concentric relationship of outer tube 40 and inner tube 42 to ensure that liquid will encircle the abrasive powder as it exits inner orifice 46.

Figure 3:
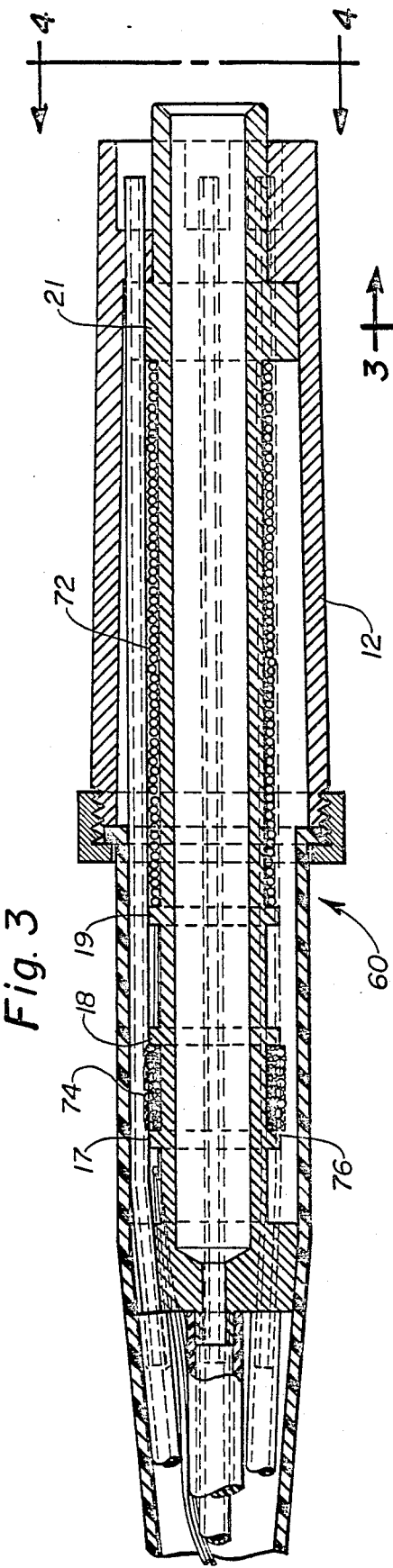
FIG. 3 is an alternative embodiment of a housing for the handpiece which provides for a choice of medicaments for irrigation.
Figure 4:
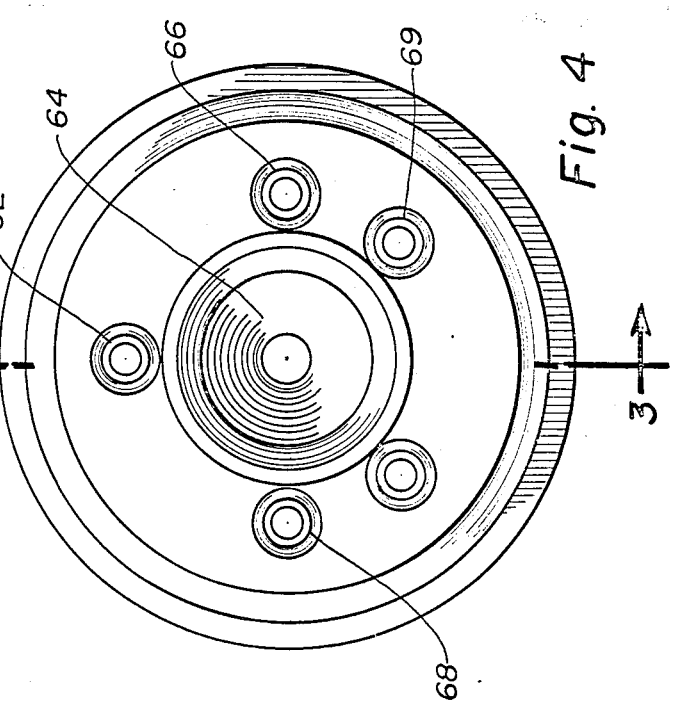
FIG. 4 is an end view of the housing of FIG. 3.

With reference now to FIGS. 3 and 4, in an alternative embodiment, the air-abrasive handpiece 60 of the invention may be provided in a cylindrical shape having means 62 within the handpiece for delivering powder, and water tube 64 for delivering water to the insert. In addition, the handpiece may be provided with additional tubes 66 and 68, or example, which can be used to deliver medicaments, or a mixture of medicaments for irrigation of the area that is to be treated with the abrasive powder. As an added feature, a water cooling flow return 69 may be provided in the handpiece for return of the water used to cool the handpiece. Such a handpiece can be used in those instances when an assured sterile water source is desired for irrigation purposes.

Although a pear shaped and a circular shaped handpiece are the illustrated embodiments, those skilled in the art will recognize that handpieces having other shapes may be provided in accordance with the invention depending on the type of material that is to be dispensed through the handpiece and the shape that is found to be most comfortable for holding.

Figure 5:
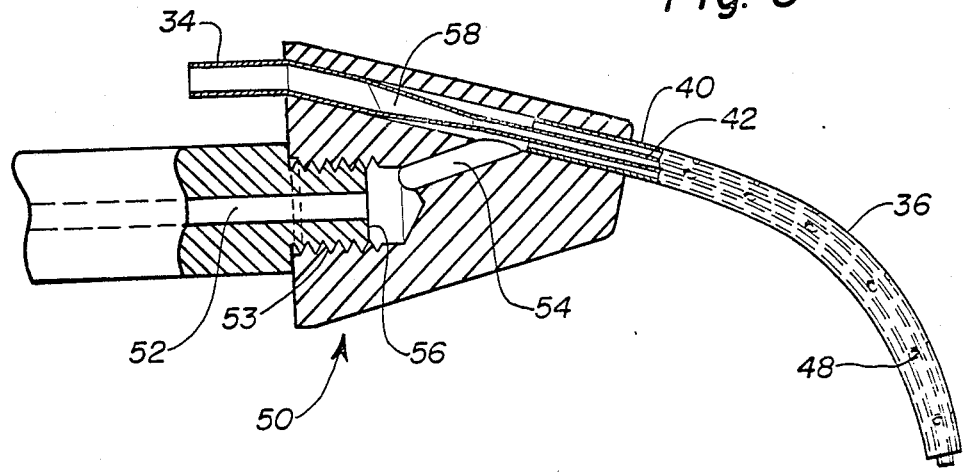
FIG. 5 is a cutaway view of a modification of the insert of FIG. 1 of the invention.

With reference now to FIG. 5, the nozzle 50 of insert 30 comprises a hole 52, or similar means, through threads 53, which permits water to pass from housing 12, past the heating element end 56 through passage 54 into outer tube 40. The heated water then passes through outer tube 40 and out of outer orifice 44.

Similarly, air and powder passes from outlet 16 in housing 12 into powder inlet 34, through tapered transition 58, through inner tube 42, and out of inner orifice 46.

Tapered transition 58 in inner tube 42 provides for a smooth transition from the large inlet tube 34 to smaller inner tube 42. The use of tapered transition 58 in tubing 42 causes the abrasive powder to flow smoothly with less clogging than is seen in prior art devices.

The housing 12 of the handpiece is adapted for sensing contact with or positioning of the particular insert being used and has means associated therewith for activating the handpiece in response to the sensing. The sensing means may be electromechanical or electrical. The response activating means may be an electromechanical switching means or an electrical switching means. In the illustrated embodiment, the sensing and switching means are electrical and electro-mechanical.

As used herein, contact is intended to include electromagnetic or electrical as well as physical contact. By electromagnetic contact, it is meant that an electromagnetic field is interrupted and/or sensed by the insert.

Those skilled in the art will recognize that the switching system may be based on changes in pneumatic pressure in the system. For example, the insert, when placed in the handpiece may cause a change in air-pressure in the handpiece which will be recognized by the system, and can be used to control the circuitry used to control the supply of materials used by the handpiece.

Figure 6:
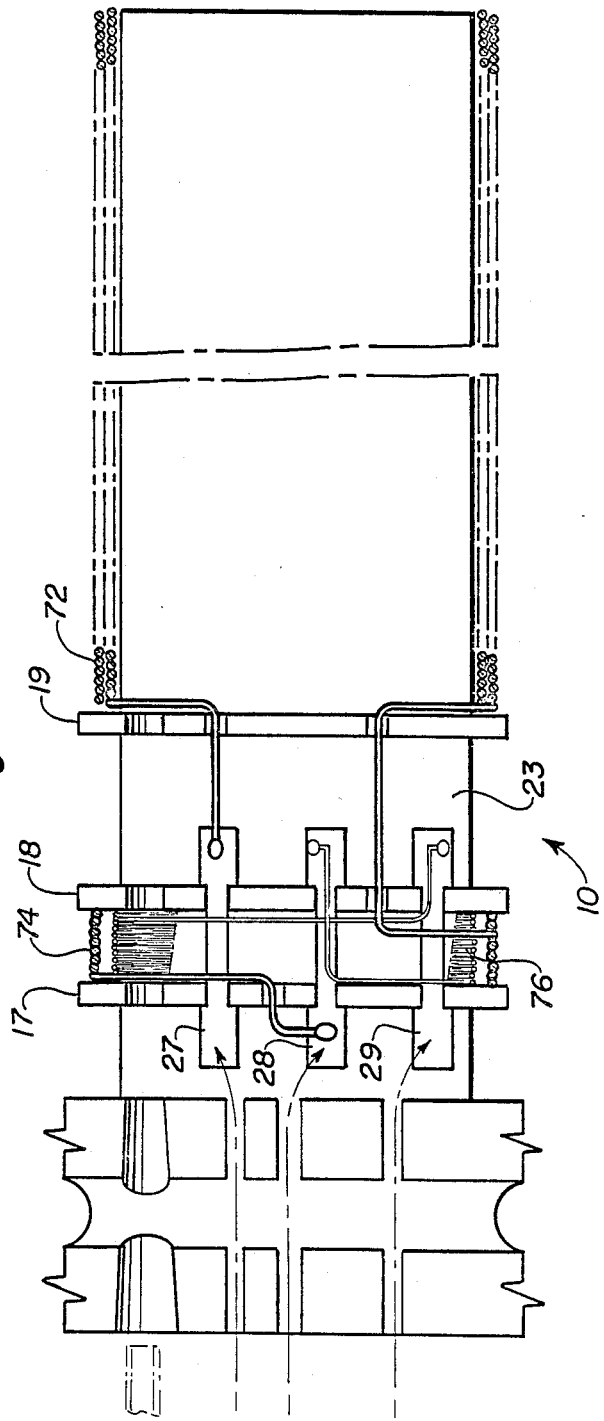
FIG. 6 is a flattened 360° illustration of the coil layout of the handpiece.
Figure 7:
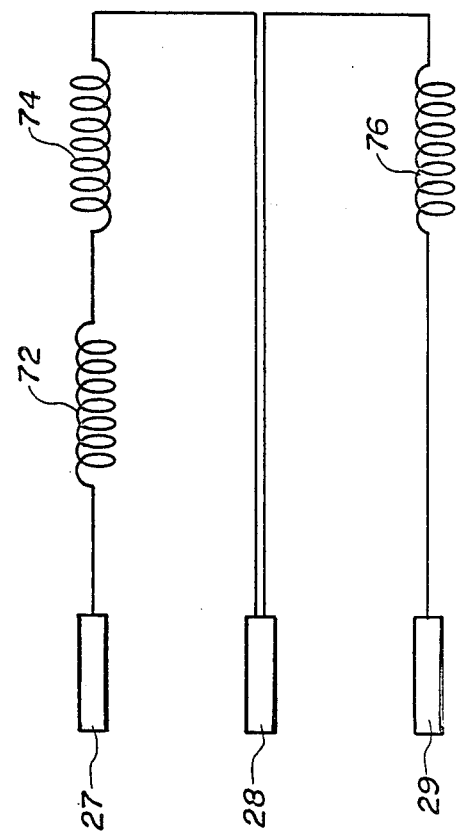
FIG. 7 is a circuit diagram of the coil circuitry of the handpiece.

With reference now to FIGS. 6 and 7, drive coil 72, which is connected to an alternating current source, is wound in a double coil between dividers 19 and 21 and establishes an alternating electromagnetic field in handpiece 10. Bucking coil 74 is provided to minimize transformer coupling between drive coil 72 and feedback coil 76. Bucking coil 74 and drive coil 72 are connected between terminals 27 and 28 in one continuous wire. Drive coil 72 is attached to terminal 27 and using a right hand turn, for example, is wound from divider 19 to divider 21 and back. The wire from drive coil 72 then traverses space 23 between dividers 18 and 19, and using a left hand turn is wound between dividers 17 and 18 to produce bucking coil 74. The end of the wire is then connected to terminal 28. Bucking coil 74 and drive coil 72 are wired in series and are wound in opposite directions and are therefore electromagnetically 180° out of phase.

Feedback coil 76 is a fine wire and is provided to register voltage developed by the movement of, for example, an ultrasonic scaler insert 20 in the electromagnetic field of handpiece 10. Feedback coil 76 is wound between dividers 17 and 18 on the handpiece, preferably before the winding of bucking coil 74, and is connected to terminals 28 (ground) and 29. The feedback coil is electrically insulated from the bucking coil.

Wires connected to terminals 27 and 29 provide the power source and register feedback, and a wire connected to terminal 28 acts as a common ground.

In the illustrated embodiment drive coil 72 comprises about 140 turns of 22 gauge wire, bucking coil 74 comprises about 9 turns of 22 gauge wire and feedback coil 76 comprises about 300 turns of 38 gauge wire.

Figure 8:
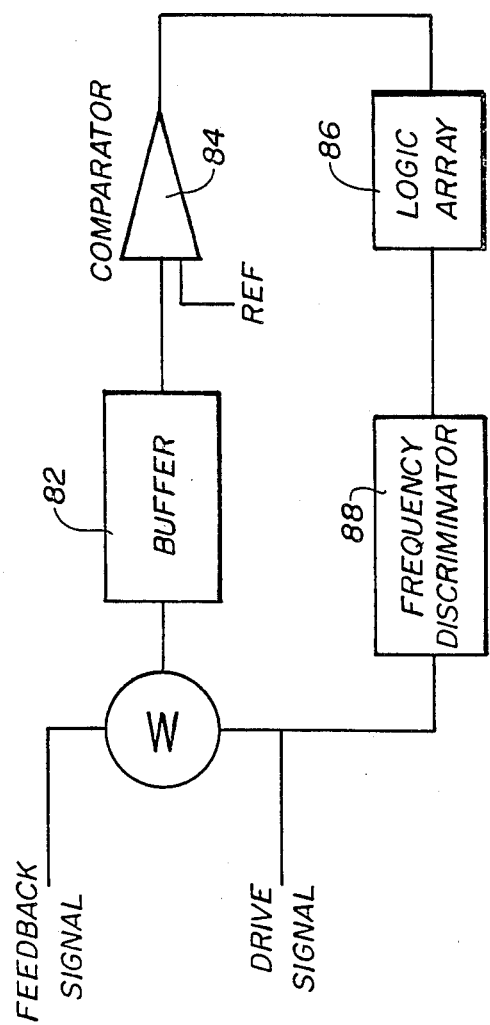
FIG. 8 is a simplified illustration in block of the circuitry and the switch mechanism of the invention.

With reference to FIG. 8, the logic circuit for controlling the dispensing of the materials used by the various inserts in handpiece 10 operates by routing transducer drive and feedback signals to a network where they are algebraically summed. The output is converted to a direct current voltage whose level is related to the status of the handpiece. When no transducer is inserted in the handpiece, a voltage in the range of 0 to 2 volts is present. When the heating insert 30 is in the handpiece, a voltage in the range of 4 to 6 volts is present. When an ultrasonic insert 20 is in the handpiece, a voltage greater than 8 volts is produced.

It will be recognized by those skilled in the art that coil windings may be changed, and inserts may be provided with different magnetic properties, and power sources may be altered to provide a wider range and a different range of feedback coil, drive coil and bucking coil voltages, and a logic array may be used to provide identification of end mode selection for a wider range of different inserts to be used with a handpiece of the invention.

The logic array circuitry and the associated switches for supplying gas, liquid and powder to the handpiece will be associated with the chassi-assembly or cabinet of the unit which is used to supply the power, gas, liquid and powder to the handpiece.

In the operation of the control circuit, the output from buffer 82 goes to voltage comparator 84 which is biased such that when a voltage in the range of 4 to 6 volts is present, the logic level of logic array 86 is high (logic 1). The logic level of logic array 86 is low (logic 0) when inputs in the range of 0 to 2 volts and greater than 8 volts are present in the circuit. A second input into the logic array comes from frequency discriminator 88. Whenever the frequency of the drive signal is within a selectable range defined by ultrasonic transducers, the output from frequency discriminator 88 to the logic array 86 is a low signal. For the heater and air-abrasive handpiece to be enabled, both of the logic conditions must be high: the frequency discriminator signal must be high, and the voltage comparator signal must be high. Accordingly, the circuits controlling delivery of air and powder will not be activated when the ultrasonic insert 20 is being used. When the circuit is enabled by the air-abrasive insert 30, the practitioner needs only to activate a foot switch or finger switch to generate heating and to activate circuitry for delivering air, abrasive powder and water to the handpiece.

Similarly, in the illustrated embodiment, if no insert is in the handpiece, the circuits will not be activated, and valves electrically controlling the flow of powder and water to the handpiece will not be opened and even if the foot switch is tripped accidentally, powder and water will not flow through housing 12. Thus, the switching system of the invention simplifies procedures for the operator, and substantially eliminates the possibility of mistakes which could necessitate a time consuming clean-up of the operatory.

When using the apparatus of the invention, the practitioner may find it most convenient to start out using the scaler insert on one area of the mouth, and follow the scaling treatment immediately with an air abrasive treatment in the same area of the mouth, and follow the same procedure in other areas of the mouth. In such a procedure, the practitioner may keep both inserts handy, and make the two or more (any number of) changes of inserts desired, without moving from the patient's side. The apparatus therefore provides for an even sequential flow in the cleaning procedure, as well as time saving for the practitioner.

Although illustrated as a magnetostrictive system, those skilled in the art will recognize that a handpiece using a switching system may be adapted to be powered using other means, such as an electrostrictive system.

In both magnetostrictive and electrostrictive systems, it is desirable to drive the transducer at its frequency of resonance. This frequency is determined in part by a complex interaction of insert length or physical dimensions, temperature characteristics of the transducer material, mechanical loading of the system and the velocity of sound in the transducer material. Since the output of the system is the mechanical stroke or vibration of the working end (tip) of the insert or transducer, the most effective method of detecting all mechanical changes of the system, e.g. the effects of temperature, loading, wear, etc., is to sense the actual movement and changes in the movement of the transducer itself. It can be demonstrated that this can be accomplished by using a velocity pickup which senses the movement of the free end of the transducer which is opposite the working tip.

The selective choosing of components used in the circuit provides the biasing of the circuit.

The following describes the basis of the control portion of this invention. When excited by an induced magnetic field, the transducer system will produce its maximum excursion at both free ends whenever the frequency of excitation corresponds to the system frequency of resonance. Associating a pickup (feedback) coil to one free end of the mechanical system will result in an electrical signal which contains both frequency and phase information. Since the pickup is sensing the motion or velocity of the transducer, the phase of the electromechanical sensor signal, depending on the components used in the circuit will be displaced by a phase angle of from 50° to 130°, a 70°–110° displacement being more preferred, and a 90° displacement being most preferred, from the drive signal. In addition to this electro-mechanical portion of the feedback, there is a concomitant purely electrical signal due to the transformer coupling action of the drive coil and the feedback coil. The signal of the feedback coil, however, is displaced from the signal of the drive coil by either 0° or 180° depending on the sense of the two windings. When the coils are both wound in the same direction, for example, the signal displacement will be about 0°, and when the windings of the two coils are wound in opposite directions, the displacement will be about 180°. It can be demonstrated that when the system's frequency of resonance is modified by temperature, wear of the mechanical parts or mechanical loading, the electromechanical phase relationship between the drive and feedback signals remains relatively constant.

In order to insure start-up of the transducer under any load condition, it is desirable for the system to lock onto the operating frequency under any load condition. After start-up, the system will adjust using the control portion of the system, to prevent stalling under the working conditions encountered, while maintaining optimum mechanical output.

The present invention has accomplished precise operational control of the electro-mechanical system by:

1. Utilizing the unmodified phase information of the velocity type pick-up.
2. Use of unique biasing of control circuits which use the phase information to self tune the center frequency of the system.

Figure 9:
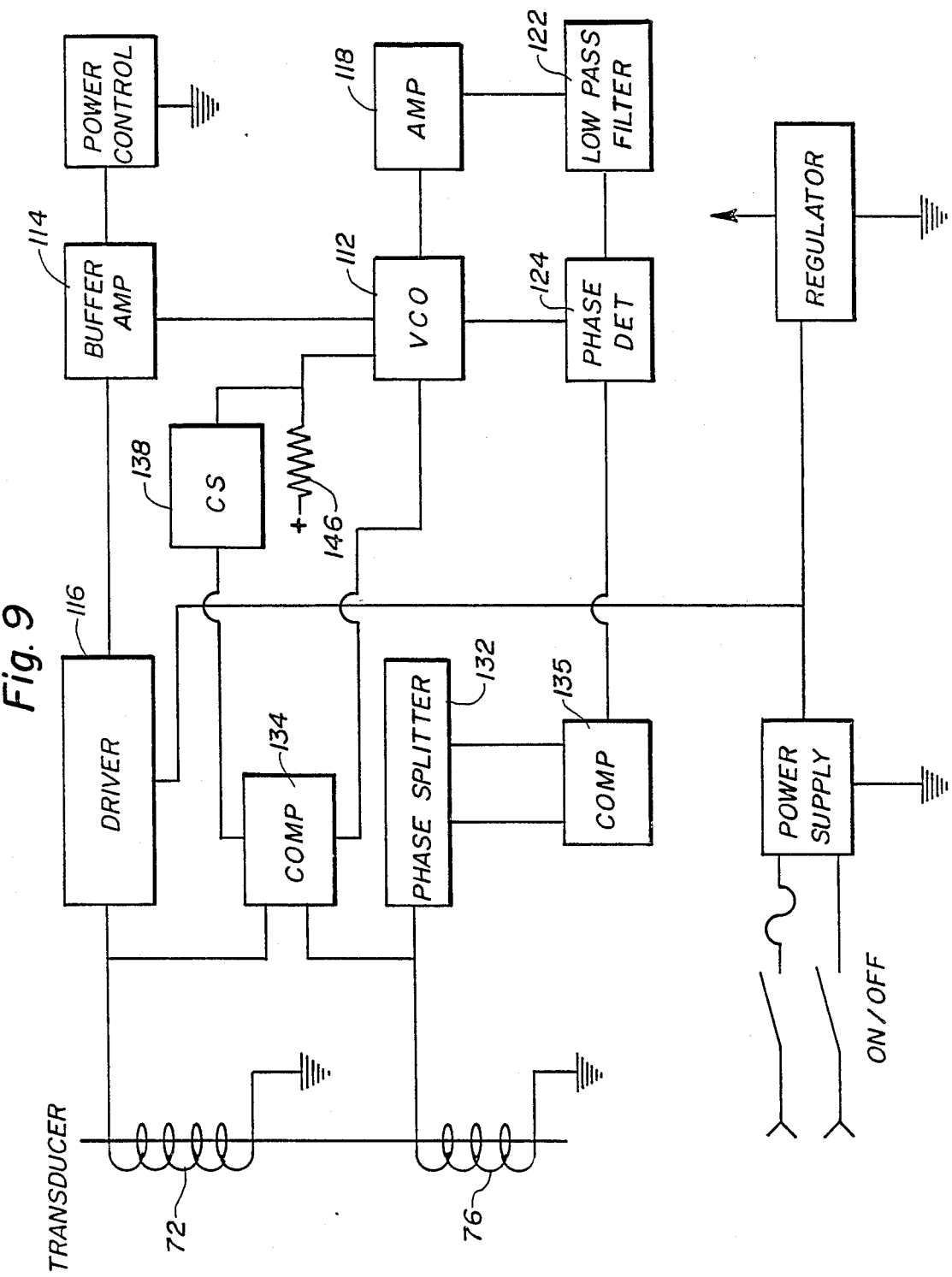
FIG. 9 is a block diagram illustrating the drive system for the transducer in the scaler insert.

With reference now to FIG. 9, when power is applied to the system the internal oscillator 112 of the phase lock section of the circuit feeds its output to the buffer amplifier 114 which isolates the phase lock from the output driver 116. The phase lock portion of the circuit comprises voltage control oscillator 112, amplifier 118, low pass filter 122, phase detector 124, phase splitter 132, comparators 134 and 135, current source 138, and fixed resistor or alternatively potentiometer 146. The driver 116 places the initial power signal on the output coil (drive coil) 72. Initially, the system starting point is determined by the value of fixed resistor or potentiometer 146.

Since the initial frequency of the system is not the frequency of resonance, the transducer will simply couple the drive signal via transformer action to the pick-up coil 76. This signal is purely electrical in nature. The feedback signal from pick-up coil (feedback coil) 76 is fed to phase splitter 132 whose algebraic difference signal is fed to comparator circuit 135. The bias on this section is such that the comparator circuit 135 uniquely preserves the phase information contained in the feedback. At this point in the sequence, phase and frequency information are present in the output signal of comparator 135. This signal is fed to the phase detector input of the phase lock circuitry. Here the signal is compared against the drive signal which is represented by the output of the voltage controlled oscillator 112.

The phase detector 124 provides an error signal for the voltage control oscillator 112. This corrected or enhanced signal is fed around the loop in the same manner as previously described. As the system approaches the correct operating frequency, the phase signal of the feedback becomes electro-mechanical in nature due to the influence of the motional feedback. When the system reaches its frequency of resonance the phase error approaches zero and the system is locked onto the maximum mechanical output point. Once the system is locked onto the true phase point, changes in operating frequency due to polarization effects, temperature, loading and insert or transducer wear will be automatically compensated since the true phase lock characteristic uses the mechanical vibration peak as its reference.

After the system is locked, the leading edge of the signal from feedback coil (pick-up coil) 76 and the trailing edge of the signal from the drive coil (output coil) 72 are processed in comparator 134, whose output is a pulse whose width is proportional to the time difference (phase difference) between these signals. The pulse is integrated and fed to a current source 138 which delivers a D.C. current to the voltage control oscillator 112 whose center frequency is modified by this current. An increase in current increases the voltage control oscillator frequency. This method has demonstrated frequency tracking over a two octave frequency range without losing lock.

Power output or amplitude control is effected by varying the current in the buffer amplifier.

The proper operation of the invention is not dependent upon the sensing of any voltage or current amplitude variations. Neither does the amplitude of the feedback signal affect the optimum operating point. In addition to advancing the art of precise frequency control over an expanded frequency and load range, this invention also represents a mechanical simplification and requires a minimum of components. Furthermore, since system control is directed by the actual vibrating system (transducer), selection of electrical and mechanical components is not critical to system operation.

Although the operation of the system was described using a phase lock circuit, its operation would be unchanged by using any control circuits that would sense the phase errors and accordingly adjust or correct the drive circuitry.

While present embodiments of the invention and methods of practicing the same have been illustrated and described, it will be recognized by those skilled in the art that this invention may be otherwise variously embodied and practiced within the scope of the following claims.

We claim:
1. A single multi-function handpiece for multiple dental treatments comprising:
    (a) a housing having a longitudinal bore therein adapted to receive a variety of dental tool inserts therein,
    (b) means in said housing for establishing an alternating electromagnetic or electrostrictive field
    (c) at least one inlet into said housing for introduction of gas therein, and
    (e) means for detecting the presence or absence of a particular insert used.
2. The single multi-function handpiece of claim 1 in which said insert comprises a transducer stack integrally connected to a dental tool and is an ultrasonic scaling insert.
3. The single multi-function handpiece of claim 1 in which said insert is an air-abrasive insert comprising a tubular member integrally connected to concentric tubing adapted for dispensing liquid and powder for stain and plaque removal.
4. The single multi-function handpiece of claim 2 in which said ultrasonic scaler insert interacts with said housing to produce a recognizable signal which is used to activate said handpiece when said insert is placed into position in said housing through circuitry in said housing.
5. The single multi-function handpiece of claim 3 in which said air-abrasive insert interacts with said housing to produce a recognizable signal which is used to activate said handpiece when said insert is placed into position in said housing through circuitry in said housing.
6. The single multi-function handpiece of claim 3 in which said alternating electromagnetic field causes heating in said insert when said field interacts with said tubular member.
7. The single multi-function handpiece of claim 1 which comprises means for introduction of powder comprising a hollow tube adjacent to and parallel to said housing.
8. The single multi-function handpiece of claim 3 in which means for introduction of a powder comprises a hollow heating element on said insert.
9. The single multi-function handpiece of claim 3 in which said insert comprises a heating element, a nozzle having concentric tubing for dispensing air-abrasive powder and liquid, and a powder inlet for receiving powder from said housing.
10. The single multi-function handpiece of claim 9 in which an inner tube in said concentric tubing is used for dispensing air-abrasive powder, and wherein said inner tube has a tapered transition from tubing in said powder inlet to smaller tubing in said concentric tubing.

11. The single multi-function handpiece of claim 3 in which a plurality of inlet tubes are provided in said handpiece for delivering irrigating fluids and medicaments.

12. A nonvibrating insert for use in a handpiece having a housing having a longitudinal bore therein adapted to receive a variety of dental tool inserts therein said handpiece having at least one inlet for the introduction of a gas therein, and means for establishing an alternating electromagnetic field in housing, said insert comprising a hollow tubular member integrally connected to a nozzle having two concentric tubes adapted for dispensing powder and liquid from said insert, said nozzle having a powder inlet extending therefrom parallel to said hollow tubular member and communicating with the inner tube of said two concentric tubes, the inner tube of said two concentric tubes having a tapered transition from one diameter to a smaller diameter, an outer tube of said two concentric tubes encircling said transition area wherein an inlet to said outer tube is provided near the tapered transition of said inner tube, said member comprising means for converting electromagnetic energy to heat electrostrictively.

13. The insert according to claim 12 in which said heating means comprises a ferrous material.

14. The insert according to claim 12 in which said heating means is plated tubular steel.

15. A circuit for selecting a driving circuit comprising:
 (a) at least one drive coil for establishing an alternating electromagnetic field, and at least one feedback coil wherein said circuit has a voltage dependant on the nature of an insert placed within the windings of said drive coil and feedback coil
 (b) a frequency discriminator for detecting the frequency of the signal produced by the drive coil, and
 (c) a logic circuit adapted to detect different voltages and different frequencies in said circuit wherein said logic circuit comprises in series a buffer for transmitting a voltage signal to a comparator, a voltage comparator for comparing a voltage signal from said buffer with an internal reference, a frequency discriminator for recognizing and signaling the frequency of the circuit, means for algebraically summing the voltage of said drive coil and the resulting voltage in said feedback coil, and a logic array wherein input from said voltage comparator and frequency discriminator determines the value of the signal produced by said logic array depending on the values of the information received.

16. A circuit for fine-tuning mechanical output in a magnetrostrictive apparatus which comprises
 (a) a housing having a longitudinal bore therein adapted to receive a variety of dental tool inserts therein,
 (b) means in said housing for establishing an alternating electromagnetic field which comprises a drive coil
 (c) and an insert in said housing, said insert comprising a transducer stack integrally connected to a scaling dental tool, said transducer stack being contained in said longitudinal bore,
said circuit comprising a feedback coil in said housing in series with said drive coil and driving circuitry, wherein said drive coil induces vibrating motion in said transducer and wherein the free vibrating end of said transducer induces a voltage in said feedback coil, said voltage being a measure of the mechanical output of said apparatus, wherein the voltage induced in said feedback coil contains both frequency and phase parameters, all of said parameters comprising a sensor signal, and wherein said sensor signal is fed to driving circuitry that controls the power input to said apparatus.

17. The insert of claim 12 which has a powder inlet attached to said nozzle, said powder inlet being adapted to receive powder from a housing of a handpiece and to provide a connection therewith.

18. The insert of claim 12 in which guide means are provided between an inner tube of said concentric tubing and an outer tube of said concentric tubing, said guide means being adapted to maintain a concentric relationship between said inner and outer tubes.

19. The switching circuit according to claim 15 in which said drive coil and said feedback coil are 180° out of phase.

20. The circuit of claim 15 in which algebraically summed voltage is converted to a direct current voltage the magnitude of which is input into a logic array.

21. The circuit of claim 20 in which a frequency discriminator provides a signal to said logic array when the frequency of the drive signal is in a range defined by ultrasonic transducers.

22. The circuit of claim 21 in which the summed voltage produces a high signal in the logic array when the magnitude thereof is 4 to 6 volts, and a low signal when the magnitude thereof is 0–2 or above 8 volts; and the frequency discrimination produces a low signal when an ultrasonic insert is used, and a high signal when an air-abrasive insert is used.

23. The circuit for fine tuning mechanical output of claim 22 in which the phase angle of said sensor signal is displaced by a phase angle of from 70°–110° from said drive signal produced by said driving circuitry.

24. The circuit for fine tuning mechanical output of claim 23 in which the phase angle of said sensor signal is displaced by a phase angle of from 70°–110° from said drive signal.

25. The circuit for fine tuning mechanical output of claim 23 in which the phase angle of said sensor signal is displaced by a phase angle of from 90° from said drive signal.

26. The circuit for fine tuning mechanical output of claim 16 which comprises an internal oscillator, a buffer amplifier, an output driver, a feedback coil, an amplifier, a low pass filter, phase detector, phase splitter, comparators, current source, and a potentiometer.

27. The circuit for fine tuning mechanical output of claim 26 in which said internal oscillator feeds its output to said buffer amplifier which isolates phase lock from the output of said driver, and the signal from said feedback coil is fed to said phase splitter whose algebraic difference signal is fed to said comparator which retains phase information contained in a signal from the feedback coil, and phase and frequency information is passed from said comparator to said phase detector where it is compared with information received from said oscillator.

28. The circuit for fine tuning mechanical output of claim 27 in which said phase detector provides an error signal for said oscillator and said signal is fed around and added to the signal in a loop comprising said oscillator, buffer amplifier, driver, feedback coil, phase splitter, comparator and phase detector until the frequency of resonance is reached.

* * * * *